United States Patent
Kim et al.

(10) Patent No.: US 9,907,861 B2
(45) Date of Patent: Mar. 6, 2018

(54) HIGH MOLECULAR WEIGHT ARGININE-GRAFTED BIOREDUCIBLE POLYMERS

(71) Applicant: University of Utah Research Foundation, Salt Lake City, UT (US)

(72) Inventors: Sung Wan Kim, Salt Lake City, UT (US); Hye Yeong Nam, Cheongju-si (KR); Kihoon Nam, Salt Lake City, UT (US); David A. Bull, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/373,312

(22) PCT Filed: Jan. 18, 2013

(86) PCT No.: PCT/US2013/022294
§ 371 (c)(1),
(2) Date: Jul. 18, 2014

(87) PCT Pub. No.: WO2013/109983
PCT Pub. Date: Jul. 25, 2013

(65) Prior Publication Data
US 2015/0057339 A1    Feb. 26, 2015

Related U.S. Application Data

(60) Provisional application No. 61/632,124, filed on Jan. 18, 2012.

(51) Int. Cl.
*A61K 47/48* (2006.01)
*A61K 48/00* (2006.01)
*C12N 15/85* (2006.01)
*A61K 47/30* (2006.01)
*A61K 47/34* (2017.01)
*C12N 15/11* (2006.01)
*A61K 47/59* (2017.01)

(52) U.S. Cl.
CPC .......... *A61K 48/0041* (2013.01); *A61K 47/34* (2013.01); *A61K 47/595* (2017.08); *C12N 15/111* (2013.01); *C12N 15/85* (2013.01); *C12N 2310/14* (2013.01); *C12N 2320/32* (2013.01)

(58) Field of Classification Search
CPC .. A61K 47/34; A61K 48/0041; C12N 15/111; C12N 15/85; C12N 2310/14
See application file for complete search history.

(56) References Cited

U.S. PATENT DOCUMENTS

| | | | |
|---|---|---|---|
| 5,578,442 A | 11/1996 | Desai et al. | |
| 8,153,154 B2 | 4/2012 | Kim et al. | |
| 8,153,155 B2 | 4/2012 | Kim et al. | |
| 2003/0232968 A1 | 12/2003 | Li et al. | |
| 2004/0209832 A1 | 10/2004 | McSwiggen et al. | |
| 2006/0204472 A1 | 9/2006 | Paleos et al. | |
| 2009/0130752 A1 | 5/2009 | Kim et al. | |
| 2009/0233365 A1 | 9/2009 | Kim et al. | |
| 2009/0297487 A1 | 12/2009 | Boe et al. | |
| 2010/0010067 A1 | 1/2010 | Kim et al. | |
| 2010/0178699 A1* | 7/2010 | Gao | A61K 9/1272 435/375 |

FOREIGN PATENT DOCUMENTS

| WO | WO 98/19710 A2 | 5/1998 |
|---|---|---|
| WO | WO 2009/102894 A2 | 8/2009 |
| WO | WO 2009/102894 A3 | 8/2009 |
| WO | WO 2014/185975 A1 | 11/2014 |

OTHER PUBLICATIONS

Choi et al. (Journal of Controlled Release, Published 2004, pp. 445-456).*
Wang et al. (BioMacromolecules, Published Feb. 18, 2011, pp. 1032-1040).*
Won at al. (The American Society of Gene & Cell Therapy, vol. 18, No. 4, pp. 734-742, published online Dec. 22, 2009.*
Choi et al.; "Enhanced transfection efficiency of PAMAM dendrimer by surface modification with L-arginine;" Journal of Controlled Release, 2004, vol. 99, pp. 445-456.
Eichman et al.; "The use of PAMAM dendrimers in the efficient transfer of genetic material into cells", Pharmaceutical Science & Technology Today, 2000, vol. 3 (7), pp. 232-245.
Kim et al.; "Arginine-grafted bioreducible poly(disulfide amine) for gene delivery systems;" 2009, Biomaterials, vol. 30; pp. 658-664.
Kim et al.; "VEGF siRNA Delivery System Using Arginine-Grafted Bioreducible Poly(disulfide amine);" American Chemical Society, Molecular Pharmaceutics; Dec. 2008.
Lee et al.; "Human erythropoietin gene delivery for cardiac remodeling of myocardial infarction in rats;" Journal of Controlled Release (2013), vol. 171, pp. 24-32.
Lee et al.; "Human Erythropoietin Gene Delivery Using an Arginine-grafted Bioreducible Polymer System;" Molecular Therapy, vol. 20, No. 7; Jul. 2012, pp. 1360-1366.
Lin et al.; "Novel bioreducible poly(amido amine)s for highly efficient gene delivery;" Bioconjugate Chemistry (2007), vol. 18, pp. 138-145.
Nam et al.; "Erythropoietin gene delivery using an arginine-grafted bioreducible polymer system;" Journal of Controlled Release (2012), vol. 157, pp. 437-444.
Nam et al.; "Paclitaxel-conjugated PEG and arginine-grafted bioreducible poly (disulfide amine) Micelles for co-delivery of drug and gene;" Biomaterials (2012), vol. 33, pp. 8122-8130.

(Continued)

*Primary Examiner* — Alma Pipic
(74) *Attorney, Agent, or Firm* — Thorpe North and Western, LLP; David W. Osborne

(57) ABSTRACT

The polymeric carrier for delivering nucleic acid material to a cell is provided herein. The polymeric carrier can include a dendrimer group having 2 to 8 termini, each of the termini having an arginine-grafted bioreducible polymer attached thereto. In one embodiment, only a portion of the termini can have an arginine-grafted bioreducible polymer attached thereto.

9 Claims, 12 Drawing Sheets

(56) References Cited

OTHER PUBLICATIONS

PCT Application No. PCT/US2009/033962: Filing date Feb. 12, 2009; University of Utah Research Foundation et al.; International Search Report dated Aug. 20, 2009.
PCT Application No. PCT/US2013/022294: Filing date Jan. 18, 2013; University of Utah Research Foundation et al.; International Search Report dated Jun. 19, 2013.
PCT Application No. PCT/US2014/00112: Filing date May 14, 2014; University of Utah Research Foundation; International Search Report dated Oct. 10, 2014.
Lee et al.; Human Erythroproietin Gene Delivery Using an Arginine-grafted Bioreducible Polymer System; Molecular Therapy; Jul. 2012; pp. 1360-1366; vol. 20, No. 7; The American Society of Gene and Cell Therapy.

* cited by examiner

PAMAM G0 + Traut's reagent PAMAM G1 → PAMAM G0-SH PAMAM G1-SH

Traut's Reagent + Primary amine molecule → Sulfhydryl-modified molecule

C2C12

HIGH MOLECULAR WEIGHT ARGININE-GRAFTED BIOREDUCIBLE POLYMERS

PRIORITY CLAIM

This application is a national stage entry of Patent Cooperation Treaty application no. PCT/US2013/022294, filed Jan. 18, 2013, which claims the benefit of U.S. Provisional Patent Application No. 61/632,124, filed Jan. 18, 2012 each of which is incorporated herein by reference.

GOVERNMENT INTEREST

This invention was made with government support under grant numbers HL071541 and HL065477 awarded by National Institutes of Health. The government has certain rights in the invention.

BACKGROUND

This invention relates to non-viral gene delivery carriers. More particularly, this invention relates to high molecular weight arginine-conjugated bioreducible poly (disulfide amine) polymers (ABP) as gene delivery carriers.

Gene therapy offers the potential to treat human congenital and acquired diseases using therapeutic gene-based drugs. One of the requirements for successful gene therapy is the development of non-toxic and efficient carriers for gene delivery. Compared to viral vectors, non-viral gene carriers such as lipids, synthetic polymers and/or peptides offer a number of advantages including easy and large-scale production, non-immunogenicity, flexible DNA and RNA loading capacity and stability among others. Despite these advantages, however, the widespread adoption of non-viral gene vectors has been limited by concerns related to cytotoxicity and decreased transfection efficiency. However, since the accumulation of non-degraded polymers inside cells is often the cause of cytotoxicity, the biodegradation of polymers after efficient transfection of DNA can reduce or eliminate this problem. Biodegradable polymers typically contain ester or disulfide-bonds. Ester bonds, however, are easily hydrolyzed in the extracellular environment, while disulfide bonds are typically more stable, as they are not reduced until they are exposed to glutathione (GSH) in the intracellular cytoplasm. Based on these considerations, several types of bio-reducible polymers containing disulfide bonds have been developed.

SUMMARY OF THE INVENTION

Arginine-grafted bioreducible polymers (ABP) were developed. Arginine modification of non-viral carriers is a promising area of investigation as the presence of arginine-rich peptides enhances the cell-penetrating ability of polymer carriers. Such ABP has been demonstrated in vitro to have a high transfection efficiency and low cytotoxicity. In vivo, however, the use of ABP is limited by the fact that it has to be used at a weight ratio above 20 for optimal transfection efficiency, a level which is associated with increased cytotoxicity. This requirement for an increased weight ratio in vivo has been attributed to the low molecular weight of ABP (approximately <5K). A polymeric gene carrier with a lower molecular weight may be less able to form compact polyplexes with the gene(s) to be delivered. The lack of formation of compact polyplexes can result in the formation of loose nanoparticles which are more susceptible to premature cleavage and gene release. This premature gene release decreases transfection efficiency compared to the polyplexes of longer and higher molecular weight polymers.

Accordingly, a polymeric carrier for delivering nucleic acid material to a cell and having low toxicity and a high transfection efficiency is provided herein. Such polymeric carrier can include a dendrimer group having 2 to 8 termini, with two or more of the termini having an arginine-grafted bioreducible polymer attached thereto. In one embodiment, only a portion of the termini have an arginine-grafted bioreducible polymer attached thereto. In another embodiment, all of the termini can have an arginine-grafter bioreducible polymer attached thereto. In a particular embodiment, the dendrimer group can have the general structure of:

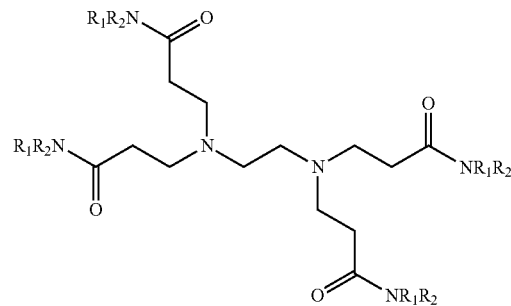

wherein each $R_1$ is individually selected from H, or $(CH_2)_2$—NH—$(CH_2)_2$—CO—NH—$(CH_2)_2$—NH—C$(NH_2)$—$(CH_2)_3$—S—S—$(CH_2)_2$—CO—NH-ABP, and each $R_2$ is individually selected from either $(CH_2)_2$—NH—C$(NH_2)$—$(CH_2)_3$—S—S—$(CH_2)_2$—CO—NH-ABP, or $(CH_2)_2$—NH—$(CH_2)_2$—CO—NH—$(CH_2)_2$—NH—C$(NH_2)$—$(CH_2)_3$—S—S—$(CH_2)_2$—CO—NH-ABP, wherein ABP has the general structure:

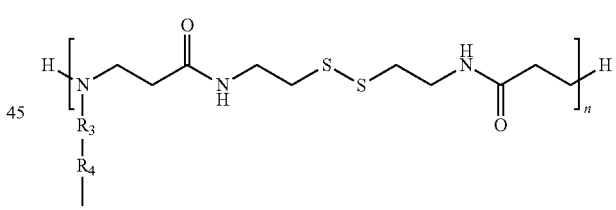

wherein n is 1 to 10 and wherein $R_3$ is $(CH_2)_m NH$, wherein m is about 1 to about 18; and $R_4$ is an arginine residue.

In another embodiment, a complex including a nucleic acid associated to a polymeric carrier for delivery of nucleic acid material to a cell is provided. The complex can include a polymeric carrier with a dendrimer group having 2 to 8 termini with all or a portion of the termini having an arginine-grafted bioreducible polymer attached thereto.

In another embodiment, a method for transfecting a cell is provided. The method includes providing any one of the complexes described herein and contacted a cell with the complex. The contacting can occur in vitro or in vivo.

BRIEF DESCRIPTION OF THE DRAWINGS

Additional features and advantages of the invention will be apparent from the detailed description which follows.

FIG. 8A shows histograms of ABP polyplexes at different weight ratios, FIG. 8B shows histograms of PAM-ABP polyplexes at different weight ratios, FIG. 8C shows representative histograms of ABP and PAM-ABP at weight ratios of 5 and 10, while FIG. 8D shows a bar graph representing the mean percentages of cellular uptake with M region gating. ** $P<0.01$.

Figure 1:
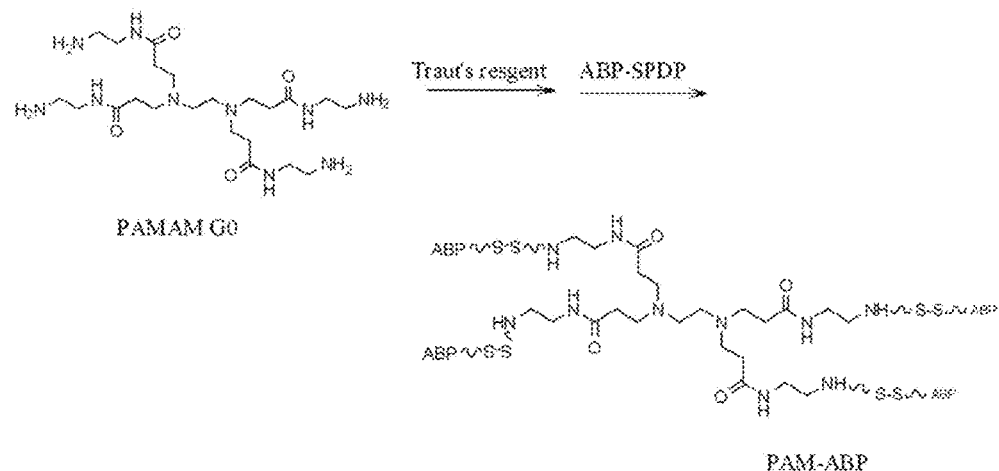
FIG. 1 shows a scheme for synthesis of an illustrative embodiment of a high molecular weight ABP polymer according to an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Before the present polymeric carriers, complexes, and methods are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "a termini" includes reference to one or more of such termini's, and reference to "the selected nucleic acid" includes reference to one or more of such nucleic acids.

Definitions

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, the term "about" is used when used in the context of a numerical range provides flexibility to the numerical range endpoint(s) by providing that a given value may be "a little above" or "a little below" the endpoint(s).

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

As used herein, "poly(CBA-DAH)" means polymers formed between cystaminebisacrylamide ("CBA") and 1,6-diaminohexane ("DAH"). Similarly, "poly(CBA-DAB)" means polymers formed between CBA and 1,4-diaminobutane ("DAB"), and "poly(CBA-DAE)" means polymers formed between CBA and 1,2-diaminoethane ("DAE").

As used herein, "siRNA" means small interfering RNA, and "RNAi" means RNA interference.

As used herein, "PEI" means polyethylenimine, "PEI25k" means polyethylenimine having a nominal molecular weight of about 25,000, and "bPEI" means branched polyethylenimine.

As used herein, "administering" and similar terms mean delivering a complex to an individual being treated such that the complex can contact and be internalized in cells, such as cancer cells. Thus, in one embodiment the complex can be administered to the individual by systemic administration, such as by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added. Other known modes of administration can also be used including, but not limited to oral administration and transdermal administration for either local or systemic delivery.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

It has been discovered that higher molecular weight ABP polymers are capable of providing higher transfection efficiency for nucleic acid materials than lower molecular weight ABP polymers. As used herein, the term "high molecular weight" or "higher molecular weight" when used to describe polymers or polymeric carriers refers to weights of 5 kDa or more. Accordingly, in one embodiment, high molecular weight ABP polymers are disclosed including a dendrimer type of ABP having a dendrimer backbone and ABP residues at the surface which can in some aspects, be used as a carrier for nucleic acid materials.

In another embodiment, a complex comprising selected nucleic acid material associated with a polymeric carrier for delivery thereof to a cell is provided. Without being limited by theory, the association between the nucleic acid material and the polymeric carrier is believed to be due to electrostatic interactions between the plasmid DNA and the polymeric carrier. The polymer carrier can include a dendrimer group having 2 to 8 termini, with one or more of the termini having an arginine-grafted bioreducible polymer attached thereto. The selected nucleic acid material to be delivered by the polymeric carrier can generally be any type of nucleic acid material including, but not limited to oligonucleotides, plasmids, siRNA, and the like. One of the advantages of the polymeric carriers disclosed herein is their ability to efficiently delivery nucleic acid material to a cell at low ratios (weight to weight W/W) of polymeric carrier to nucleic acid material. In one embodiment, the polymeric carrier can be such that, when present in a complex with a nucleic acid material, the ratio (W/W) of polymeric carrier to selected nucleic acid material is about 5 or less. In another embodiment, the ratio (W/W) of polymeric carrier to selected nucleic acid material is about 3 or less. In still a further embodiment, the ratio (W/W) of polymeric carrier to selected nucleic acid material is about 2 or less.

In still another embodiment, a method for transfecting a cell is provided. The method includes providing any one of the complexes described herein and contacted a cell with the complex. The contacting can occur in vitro or in vivo. In one embodiment, the cell is a mammalian cell.

It is noted that when discussing a polymer carrier for delivery of nucleic acid material, a complex for delivering nucleic acid to a cell, or a method for transfecting a cell, each of these discussions can be considered applicable to the other embodiments, whether or not they are explicitly discussed in the context of that embodiment. Thus, for example, in discussing an dendrimer as a component of a polymer carrier for delivery of nucleic acid material, such dendrimer discussion can also be used in association with the complex for delivering nucleic acids to a cell and the method of transfecting a cell, and vice versa.

In one embodiment, a polymeric carrier for delivery of nucleic acid material to a cell is provided which includes a dendrimer group having 2 to 8 termini, at least one of the termini having an arginine-grafted bioreducible polymer attached thereto. Generally, any known dendrimer group having 2 to 8 termini can be used although it is preferable that the dendrimer be a biocompatible composition. In one embodiment, the dendrimer group of the polymeric carrier can have at least 4 termini. In another embodiment, the dendrimer group can have at least 8 termini. In another embodiment, at the dendrimer can have at least 4 termini and at least 4 of the termini have an ABP residue attached thereto. The high molecular weight polymeric carrier can have a molecular weight of about 5 kDa to about 50 kDa. In one embodiment, the polymeric carrier can have a molecular weight of about 9 kDa to about 50 kDa.

Figure 10:
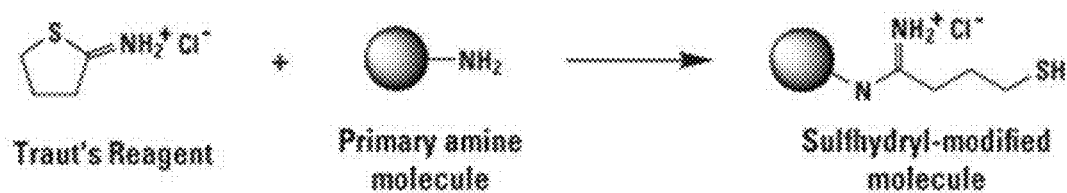
FIG. 10 shows a general reaction scheme for the formation of G0 and G1 PAM-ABP polymeric carriers in accordance with one embodiment of the present invention.
Figure 11:
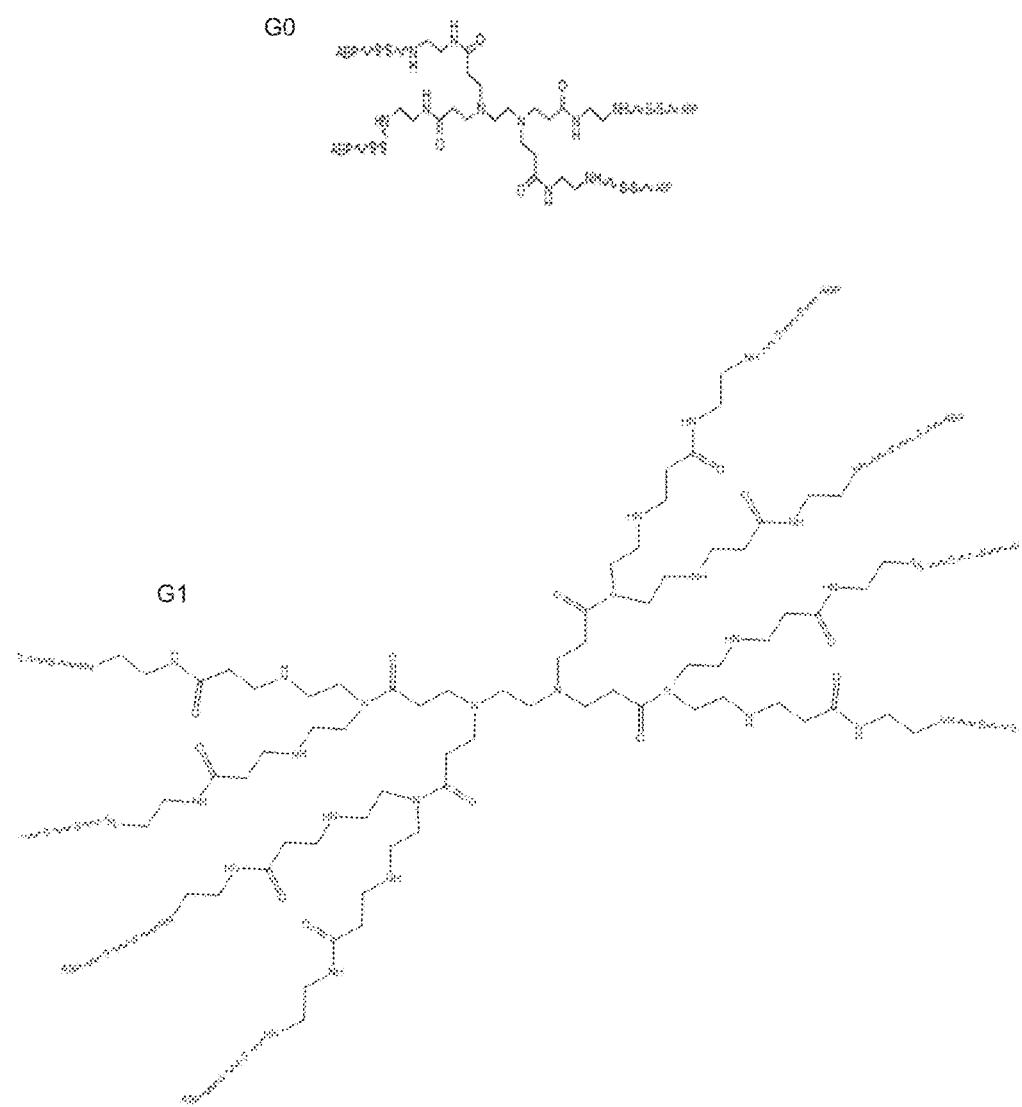
FIG. 11 shows general structures for PAM-ABP G0 and G1 polymeric carriers in accordance with embodiments of the present invention.

In one embodiment, the dendrimer group can have the general structure of:

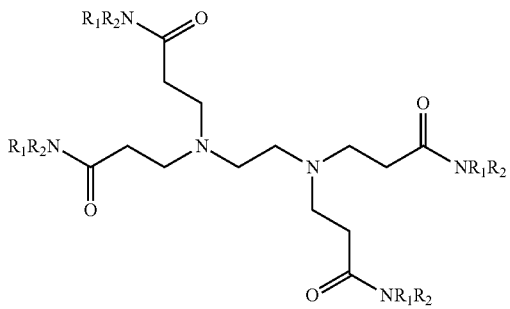

with each $R_1$ being individually selected from H, or $(CH_2)_2$—NH—$(CH_2)_2$—CO—NH—$(CH_2)_2$—NH—C(NH_2)—$(CH_2)_3$—S—S—$(CH_2)_2$—CO—NH-ABP, and each $R_2$ being individually selected from either $(CH_2)_2$—NH—C(NH_2)—$(CH_2)_3$—S—S—$(CH_2)_2$—CO—NH-ABP or $(CH_2)_2$—NH—$(CH_2)_2$—CO—NH—$(CH_2)_2$—NH—C(NH_2)—$(CH_2)_3$—S—S—$(CH_2)_2$—CO—NH-ABP. It is noteworthy that the ABP component of the polymer can have the general structure:

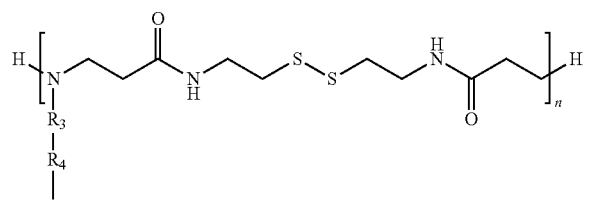

wherein n is 1 to 10 and wherein $R_3$ is $(CH_2)_m NH$, wherein m is about 1 to about 18; and $R_4$ is an arginine residue. FIG. 11 shows additional embodiments of both generation 0 (G0) and generation 1 (G1) dendrimer structures that can be used as polymeric carriers and complexes in accordance with the present invention. FIG. 10 provides a generalized description of one embodiment of the reaction scheme for forming an embodiment of the disclosed polymeric carrier.

The arginine-grafted bioreducible polymer which forms a portion of the polymer carrier or complex can have the general structure set forth below:

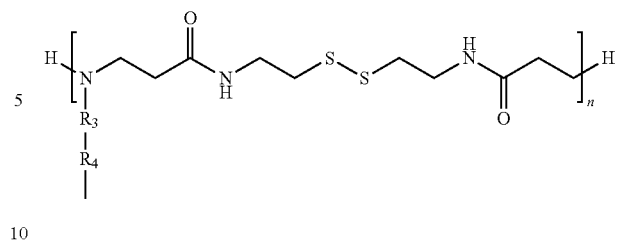

wherein n is 1 to 10 and wherein $R_3$ is $(CH_2)_m NH$, wherein m is 1 to 18; and $R_4$ is an arginine residue. In one embodiment, m can be 2 to 8. In another embodiment, m can be 6. In still another embodiment, n can about 4 to 8.

In one embodiment, the polymeric carrier can have the structure:

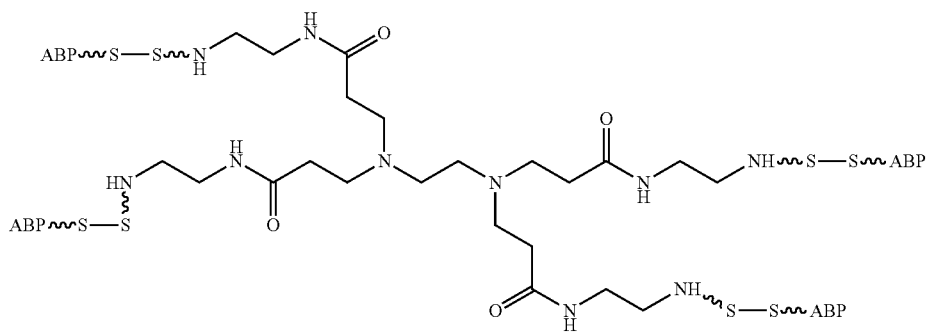

wherein

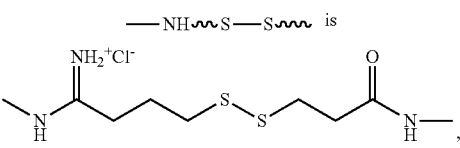

and
wherein ABP has the general structure:

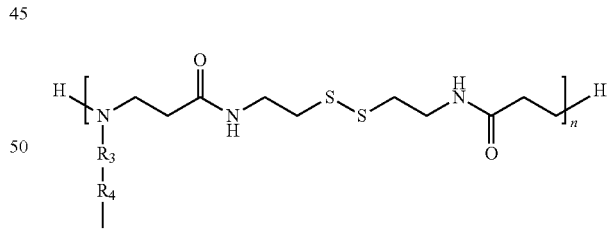

wherein n is 1 to 10 and wherein $R_3$ is $(CH_2)_m NH$, wherein m is about 1 to about 18; and $R_4$ is an arginine residue.

EXAMPLES

The following examples are provided to promote a more clear understanding of certain embodiments of the present invention, and are in no way meant as a limitation thereon.
Materials
The following materials are used in one or more of the examples described herein. Specifically, hyperbranched poly(ethylenimine) (bPEI, Mw=25 kDa), tert-butyl-N-(6-aminohexyl) carbamate (N-Boc-1,6-diaminohexane, N-Boc- DAH), trifluoroacetic acid (TFA), triisobutylsilane (TIS), DL-buthionine-sulfoxamine (BSO), and 3-[4,5-dimethylthiazol-2-yl]-2,5-diphenyltetrazolium bromide (MTT) were purchased from Sigma-Aldrich (St. Louis, Mo.). N,N'-Cystaminebisacrylamide (CBA) was purchased from Poly-Sciences, Inc. (Warrington, Pa.). Plasmid DNA encoding firefly luciferase (pLuc) or green fluorescent protein (pGFP) was purchased from Aldevron, Inc. (Fargo, N. Dak.). The Luciferase assay system and reporter lysis buffer were purchased from Promega (Madison, Wis.). Traut's reagent, SPDP and BCA protein assay kits were purchased from Pierce (Rocford, Ill.). All cell culture products including fetal bovine serum (FBS), Dulbecco's phosphate buffered saline (PBS), antibiotics, trypsin-EDTA and Dulbecco's modified Eagle's medium (DMEM) were obtained from Invitrogen (Gibco BRL, Carlsbad, Calif.). YOYO-1 iodide (1 mM solution in DMSO) and SYBR safe DNA gel stain were also purchased from Invitrogen (Carlsbad, Calif.).

Where results of an analysis are provided, the results are expressed as mean values±standard deviation (SD). Differences between groups were assessed by one-way analysis of variance (ANOVA) using SPSS 12.0 software (SPSS Inc., Chicago, Ill., USA). One-way ANOVA followed by Tukey post hoc analysis was used to identify significance between groups.

Example 1—Synthesis of PAM-ABP Polymers

ABP was synthesized as described in U.S. Pat. Nos. 8,153,154 and 8,153,155, each of which is incorporated herein by reference. The synthesized and purified ABP was dissolved in 0.1 M phosphate buffered saline (pH 7.2, 0.15 M NaCl). A 1.2 molar excess of SPDP dissolved in DMF (6.2 mg/mL) was added to the ABP solution. The mixture was stirred for one hour at room temperature, and then dialyzed against ultrapure water using a dialysis membrane (MWCO=1,000 Da, Spectrum Laboratories, Inc., Rancho Dominguez, Calif.), followed by lyophilization. For the thiolation of PAMAM, PAMAM was dissolved in 0.1 M phosphate buffered saline (pH 8.0, 0.15 M NaCl, 2.0 mM EDTA). Eight equivalents of Traut's reagent per surface primary amines of PAMAM G0 were added to the PAMAM solution with stirring, and the mixture was further reacted for one hour. The product was dialyzed against ultrapure water using a dialysis membrane (dialysis membrane (MWCO=500 Da) and the product PAMAM-SH was then lyophilized. To a prepared PAMAM-SH solution in 50 mM phosphate buffered saline (pH 7.2, 0.15 M NaCl, 10 mM EDTA), 4.4 equivalents of ABP-SPDP were added and the reaction mixture was stirred for four hours at room temperature. The reaction was monitored by UV spectroscopy at 343 nm for the presence of released pyridine-2-thione. The mixture was dialyzed against pure water with a dialysis membrane (MWCO=3,500 Da), followed by lyophilization. The synthesis of PAM-ABP was confirmed by $^1$H NMR (400 MHz, $D_2O$).

The general reaction scheme of the synthesis is shown in FIG. 1, with the four primary amines of PAMAM being modified with Traut's reagent, and the thiol groups of the modified PAMAM being reacted with SPDP linked ABP. The reaction was monitored by Thin-Layer Chromatography (TLC) with ninhydrin staining and UV spectroscopy for the presence of released pyridine-2-thion, which has a maximum extinction at 343 nm. The conjugation of ABP to the PAMAM was confirmed by proton NMR spectra, with four representative peaks for PAMAM (3.5, 3.1, 2.7, 2.4 ppm) as well as representative peaks for the arginine of ABP (1.6~1.2 ppm). Based on the results of the TLC staining, UVmeasurements, and NMR spectra, it was determined that four ABPs had been conjugated to the four primary amines of PAMAM (generation 0 (G0)). It is noted that this same technique can also be used for PAM-ABP polymers wherein the PAMAM is a generation 1 G1 dendrimer having eight termini with primary amines.

Figure 2:
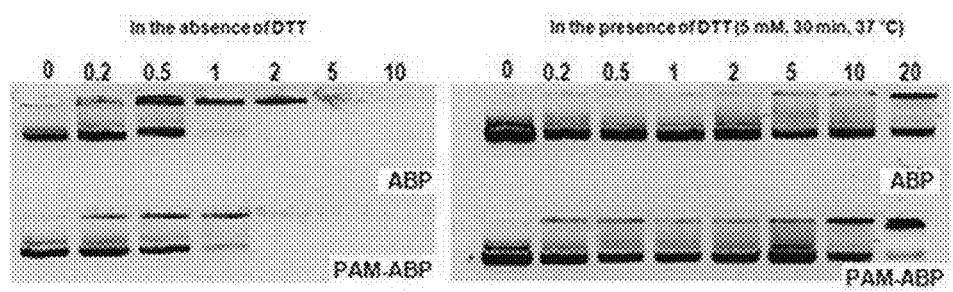
FIG. 2 shows the results of agarose gel electrophoresis of ABP and PAM-ABP polyplexes at different weight ratios with and without 5.0 DTT according to an embodiment of the invention. The numbers refer to the mean weight ratios of the polyplexes.

Example 2—Preparation, Gel Retardation Assay, and Zeta-Potential Values for Polyplexes Polyplexes were prepared by vortexing a pDNA solution with an equal volume of polymer solution in Hepes buffered saline (10 mM Hepes, 1 mM NaCl, pH 7.4) at various weight ratios, followed by incubation for 30 min. In order to examine the condensing ability of PAM-ABP with plasmid DNA at different weight ratios, a gel-retardation assay was performed. In order to compare the degree of DNA release, each polyplex was incubated in the presence of 5 mM DTT for 30 min at 37° C. The samples were then analyzed by gel electrophoresis as described below. An agarose gel (0.8%, w/v) containing an SYBR gel staining solution was prepared in TAE (10 mM Tris/HCl, 1% (v/v) acetic acid, 1 mM EDTA) buffer. Loading dye was added to each polyplex sample, and the mixtures were loaded onto an agarose gel and electrophoresed at 100 V for 30 min. The migration of DNA bands was visualized by a UV illuminator using a Gel Documentation System (Bio-Rad, Hercules, Calif.). As shown in FIG. 2, the PAM-ABP completely retarded the electrophoretic mobility of the pDNA at a weight ratio of 2, while the ABP alone did not demonstrate complete retardation until a weight ratio above 5, confirming that the PAM-ABP condenses pDNA at a lower weight ratio and more effectively than ABP alone.

Figure 3:
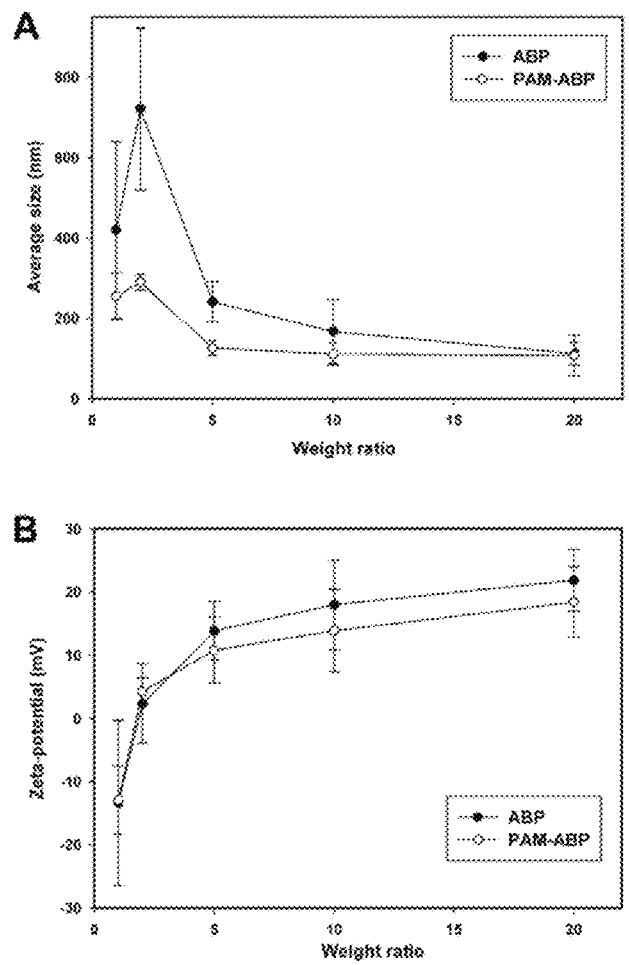
FIGS. 3A and 3B show the average size (3A) and zeta potential value (3B) of ABP polyplexes and PAM-ABP polyplexes in certain embodiments of the invention.

The particle size and zeta-potential values of the polyplexes were measured using a Nano ZS (ZEN3600, Malvern Instruments) with a He—Ne ion laser (633 nm). Fifty micro-liters of polyplex solution (0.5 µg of pDNA) were prepared at weight ratios (polymer/pDNA) ranging from 1 to 40. After 30 min incubation, the polyplex solutions were diluted in filtered water to a final volume of 600 µL before measurement. Zeta-potential values and particle sizes of the ABP and PAM-ABP polyplexes provide details of complex formation. As shown in FIG. 3, at a weight ratio of 5, the surface charge and average particle size of the ABP polyplexes were determined to be +13.0 mV and 242 nm, respectively, while the PAM-ABP formed polyplexes with a zeta-potential value of +11.0 mV and a particle size of 126 nm. These results indicate that the PAM-ABP has the physical characteristics to form more compact polyplexes than ABP alone.

Example 3—Degradation Study of PAM-ABP Polyplexes

The degradation patterns of the PAM-ABP polyplex under reductive conditions were determined by picogreen assay. Each polyplex at a fixed weight ratio was incubated in the presence of 5 mM DTT at 37° C. The picogreen reagent was added at the indicated time intervals and further incubated for 2 min. Fluorescence was measured using a Qubit® 2.0 Fluorometer (Invitrogen). DTT is a well-known reducing agent that mimics the reductive environment of the intracellular cytoplasm where the disulfide bonds of bio-reducible polymers, such as ABP and PAM-ABP, are degraded. The rate of reduction of these disulfide bonds regulates the degree of DNA release from the polyplexes, and subsequent gene expression. As shown in FIG. 2, 70% of the pDNA was released from the ABP polyplex at a weight ratio of 20 in the presence of DTT. In the case of PAM-ABP, only 5% of the pDNA was released from the polyplexes at a weight ratio of 20 in the presence of DTT.

Figure 4:
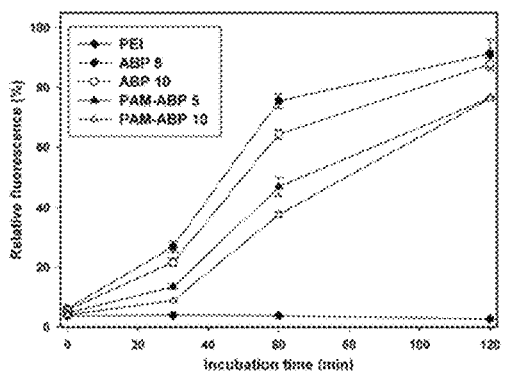
FIG. 4 shows the relative degradation of various polyplexes with 5.0 mM DTT using a picogreen assay according to one embodiment of the present invention.

For more precise analysis of the DNA release from the polyplexes in the presence of a reducing agent, a picogreen assay was carried out at weight ratios of 5 and 10 (FIG. 4). At a weight ratio of 5, the ABP formed a less compact polyplex than the PAM-ABP. Both polymers condensed pDNA successfully at a weight ratio of 10. With increasing incubation time with DTT, the ABP polyplexes displayed a more rapid increase in the release of pDNA than the PAM-ABP polyplexes. Summarizing these findings, the polyplexes of the low molecular weight ABP are more rapidly degraded in a reductive environment than the higher molecular weight PAM-ABP. The PAM-ABP forms compact and nanosized polyplexes with pDNA at a lower weight ratio and maintains more stable polyplexes in a reductive environment, allowing for more controlled carrier gene release.

Example 4—In Vitro Transfection of Polyplexes

Various types of cells were seeded in 24-well plates at a density of $5.0 \times 10^4$ cells/well and incubated in the absence or presence of buthionine-sulfoximine (BSO) for 24 h (around 70-80% confluence) in DMEM media containing 10% Fetal Bovine Serum (FBS) at 37° C. Plasmid DNA (0.5 µg/well) was complexed with polymer at different weight ratios and incubated for 30 min. The cells were then treated with the polyplexes for 4 h, after which the medium was exchanged with fresh medium containing 10% FBS and the cells incubated for 2 days before analysis. For the luciferase analysis, the cells were rinsed with DPBS and treated with 200 µL of reporter lysis buffer, followed by shaking for 30 min at room temperature. The luciferase activity of 25 µL cell lysate was measured by using 100 µL of luciferase assay reagent on a luminometer (Dynex Technologies Inc., Chantilly, Calif.). All experiments were performed in triplicate. The degree of GFP expression was measured using an EVOS microscope (AMG, Bothell, Wash.).

Figure 5:
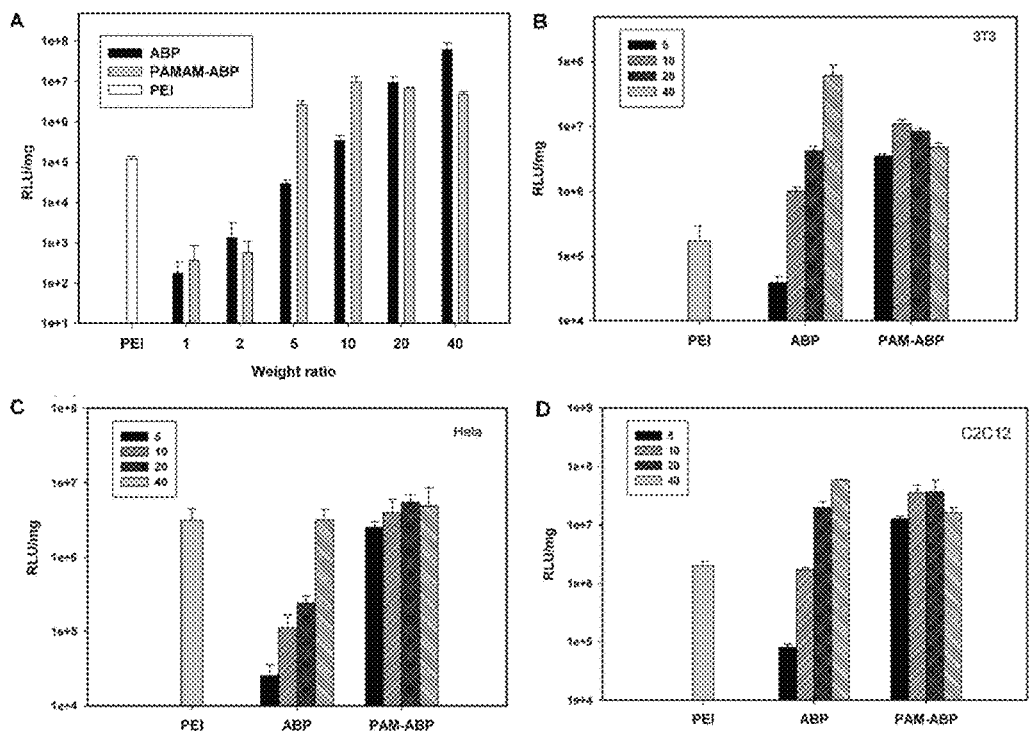
FIG. 5A-D show the relative transfection efficiencies of various polymeric polyplexes including ABP, PEI, and PAM-ABP with different cell types with FIG. 5A being NIH 3T3 cells at various weight ratios, FIG. 5B being NIH 3T3, FIG. 5C with Hela cells, and FIG. 5 D with C2C12 cells in DMEM media containing 10% fetal bovine serum (FBS) in accordance with embodiments of the present invention. The small numbers in the boxes of each figure refer to the mean weight ratios of the polyplexes. Branched PEI25 was used at a weight ratio of 1.
Figure 6:
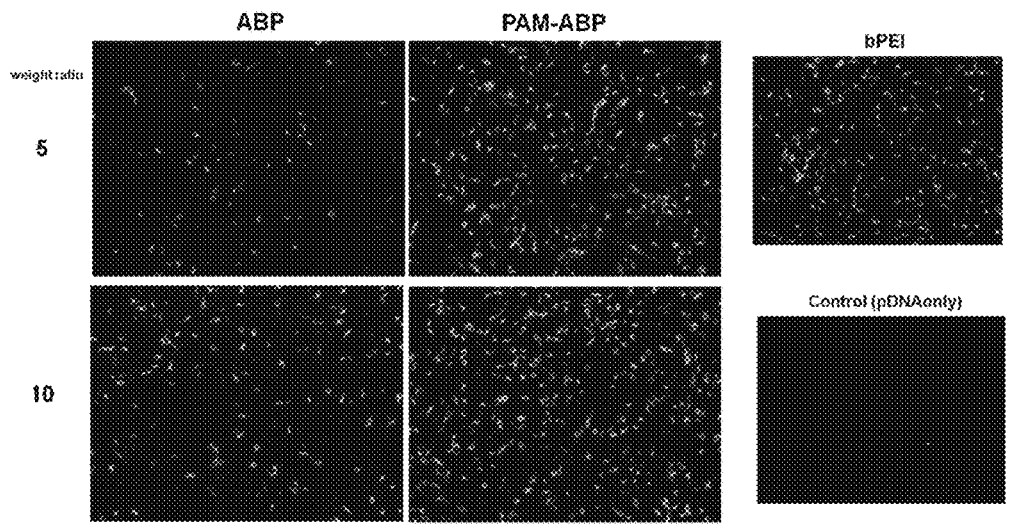
FIG. 6 shows microscopic images of ABP and PAM-ABP polyplex expression of pGFP transfection in C2C12 cells in accordance with one embodiment of the present invention. Branched PEI25k was used at a weight ratio of 1.

The transfection efficiency of the newly synthesized bio-reducible PAM-ABP was compared to the transfection efficiency of ABP in HeLa, C2C12 and NIH 3T3 cells in DMEM media containing 10% Fetal Bovine Serum (FBS) using firefly luciferase and green fluorescent protein (GFP) expression. The polymer carrier PEI was used as a control for these experiments. To determine the optimal weight ratio of PAM-ABP for gene delivery, the transfection experiments were carried out at a series of weight ratios in NIH 3T3 cells. Luciferase expression increased in a dose-dependent manner for both polymers in NIH 3T3 cells (FIG. 5A). While ABP demonstrated good transfection efficiency above a weight ratio of 20, the PAM-ABP demonstrated a similar transfection efficiency beginning at a significantly lower weight ratio of 5 and continuing on up to a weight ratio of 40. As shown in FIG. 5, at a weight ratio of 5, the transfection efficiency of PAM-ABP was almost 100 fold higher than ABP and PEI in all three cell types. Without wishing to be bound by theory, it is speculated that at least one reason for such increase is likely due to the ability of PAM-ABP to form more compact polyplexes as described above. Similar results were seen with GFP expression in C2C12 cells when comparing gene delivery using PAM-ABP to delivery using ABP alone at weight ratios of 5 and 10 (FIG. 6). These results indicate that the dendrimer ABP derivative, PAM-ABP, greatly enhances the transfection efficiency of pDNA at a lower weight ratio of polymer compared to ABP.

Example 5—Cytotoxicity of Polymers and Polyplexes

In order to evaluate the cytotoxicity of PAM-ABP and ABP, an MTT assay was performed. PEI was used as a control. To assess the cytotoxicity of the polyplexes, the cells were seeded in 24-well plates at a density of $5.0 \times 10^4$ cells/well and incubated for 24 h in DMEM medium containing 10% FBS at 37° C. Polyplexes were prepared and treated using the same protocol as the transfection experiments. After 48 h incubation, 50 µL of stock solution of MTT (2 mg/mL in PBS) was added into each well and incubated for 2 h at 37° C. The medium was then removed and 200 µL DMSO was added to dissolve the formazan crystal formed by viable cells. Similarly, to assess the cytotoxicity of the polymers, the cells were seeded in a 96-well culture plate at $1.0 \times 10^4$ cells/well in 90 µL DMEM medium containing 10% FBS. After 24 h incubation, cells were treated with 10 µL of the polymer solutions at different concentrations for 4 h in a DMEM medium without serum. After exchange of medium with fresh DMEM with 10% serum, the cells were further maintained for 48 h. Then, 25

μL of stock solution of MTT (2 mg/ml in PBS) were added to each well. After 2 h of incubation at 37° C., the medium was removed carefully and 150 μL of DMSO was added to each well to dissolve the formazan crystal. The absorption was measured at 570 nm using a microplate reader (Model 680, Bio-Rad Laboratory, Hercules, Calif.), and the cell viability was calculated as a percentage relative to untreated control cells.

Figure 7:
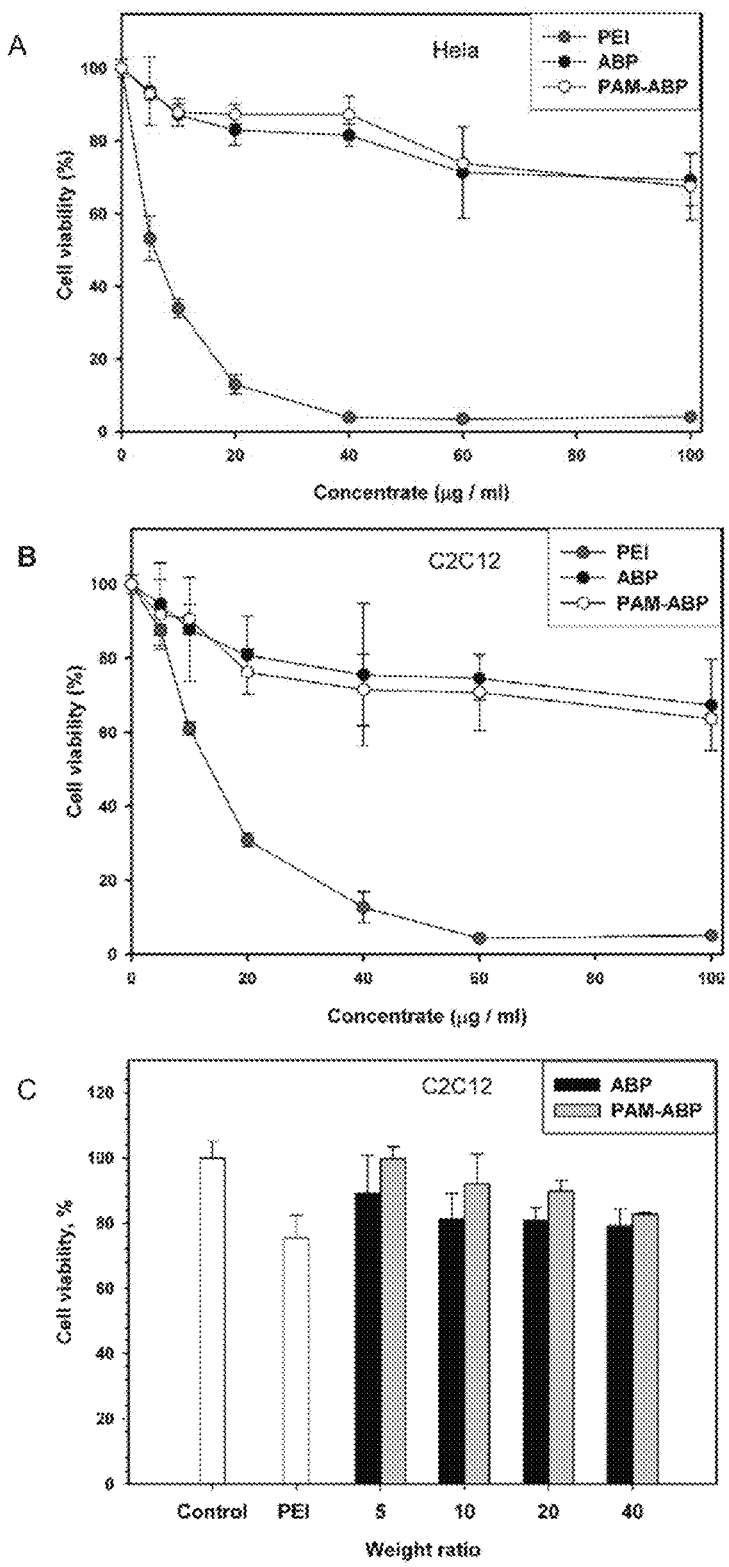
FIG. 7A-C shows the results of cytotoxicity assays for PEI, ABP, and PAM-ABP in HeLa cells (FIG. 7A), C2C12 cells at various concentration of polymers (FIG. 7B), and in C2C12 cells at various weight ratios of polyplexes by MTT assay, in accordance with embodiments of the present invention. The results are reported in relative cell viability (%).

As shown in FIGS. 7A and 7B, the relative viability of HeLa and C2C12 cells treated with PEI was less than 20%, even at very low polymer concentrations (20 μg/mL). Both PAM-ABP and ABP demonstrated low levels of cytotoxicity, with approximately 80% of cells being viable up to a polymer concentration of 60 μg/mL. Approximately 60% of cells remained viable up to an even higher polymer concentration of 100 μg/mL. The cytotoxicity of the polyplexes based on weight ratio was examined by an MTT assay in C2C12 cells. Both the PAM-ABP and ABP polyplexes were consistently associated with cell viabilities above 80% from weight ratios as low as 5 to weight ratios as high as 40 (FIG. 7C). The optimal polycationic polymer for gene delivery carrier should combine high transfection efficiency with low cytotoxicity. By this measure and the fact that PAM-ABP is efficacious at lower doses, PAM-ABP appears to be a superior carrier for gene delivery compared to ABP.

Example 6—Cellular Uptake Using Flow Cytometry

The cellular uptake of the PAM-ABP polyplexes with YOYO-1 intercalated plasmid DNA was determined by flow cytometry using PEI as a control. C2C12 cells were seeded at a density of $1.0 \times 10^5$ cells/well in a 12-well plate in DMEM medium containing 10% FBS and grown for 24 h. pDNA was labeled with YOYO-1 iodide (1 molecule of the dye per 50 base pairs of nucleotide) for 30 min before use. The polyplexes were prepared with YOYO-1 labeled plasmid DNA (pDNA 1.0 μg) and the polymers at the designated weight ratios and incubated for 30 min. The polyplexes were added to the cells and incubated for 4 h at 37° C. in serum-free medium. After removing the medium, the cells were washed with cold PBS, trypsinized and collected by centrifugation. The collected cells were suspended in 500 μL, of cold PBS, and the degree of cellular uptake was examined using a BD FACScan analyzer.

Figure 8:
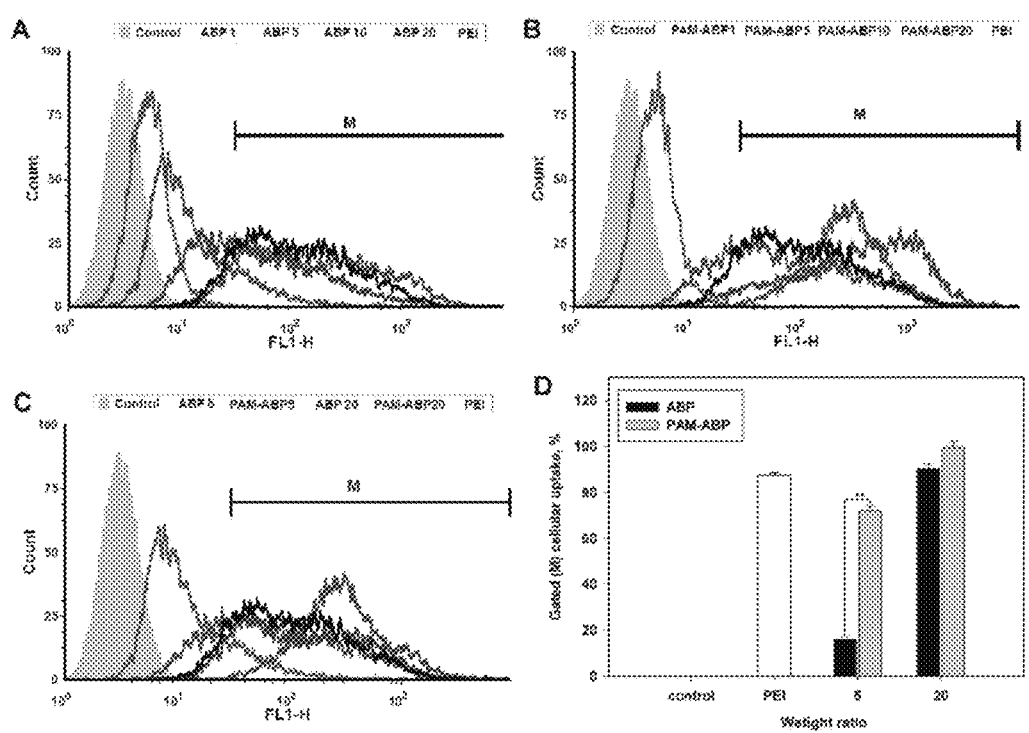
FIG. 8A-D shows flow cytometric analyses of cellular uptake assay in C2C12 cells for some embodiments of the present invention. Specifically.

As shown in FIG. 8, the cellular uptake of both the PAM-ABP and ABP polyplexes increased as the weight ratio increased. While there was a slow increase in uptake of the ABP polyplexes with increasing weight ratio, the uptake of the PAM-ABP polyplexes increased sharply at a weight ratio of 5. In order to compare the relative uptake of DNA by ABP and PAM-ABP, the quantitative cellular uptake of the polyplexes was calculated as a percentage of cell counts in the M gated region (FIG. 8D). Both polyplexes exhibited similar gating values and greater cellular uptake than PEI at a weight ratio of 20. Notably, at a weight ratio of 5, there was significantly higher uptake of the PAM-ABP polyplexes (~80%) than the ABP polyplexes (below 20%). These results suggest that the ability of PAM-ABP to form compact polyplexes enhances its cellular uptake, resulting in an increase in transfection efficiency compared to ABP.

Example 7—Investigation of Cellular Gene Delivery

Figure 9:
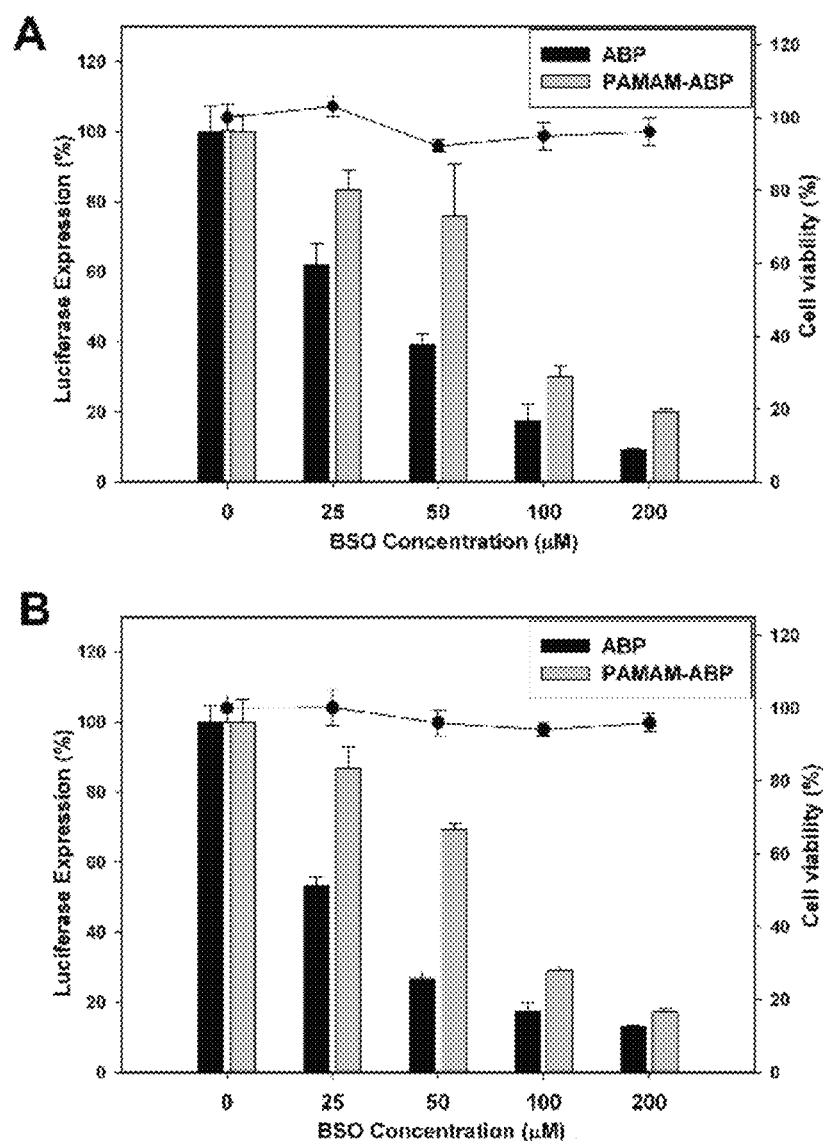
FIG. 9A-B shows luciferase expression and cytotoxicity for exemplary embodiments of the present invention after treatment with BSO, an inhibitor of GSH synthetase, in (A) MCF-7 cells and (B) A549 cells.

PAM-ABP and ABP are bio-reducible polymers with an internal disulfide bond, which is degraded in the reductive environment of the intracellular cytoplasm. The concentration of intracellular glutathione (GSH) determines the degree of reduction of the disulfide bonds in bio-reducible polymers such as PAM-ABP and ABP. To determine the impact of the reductive environment on the transfection efficiency of the polymers, the ability of the polymers to transfect cells was measured after treatment with DL-buthionine-sulfoxamine (BSO), a glutathione-depleting agent. As depletion of GSH can lead to cell death, toxicity testing was performed. Treatment with BSO was toxic to C2C12 cells, resulting in 80% cell viability at 50 μM of BSO and 40% cell viability at 100 μM of BSO (data not shown). BSO, however, was much less toxic to a breast cancer cell line (MCF-7) and human lung adenocarcinoma epithelial cell line (A549), with greater than 95% of cells remaining viable, even at a concentration of BSO as high as 200 μM. As shown in FIG. 9, the luciferase expression for both the PAM-ABP and ABP polyplexes was decreased in a BSO dose-dependent manner. ABP showed a significantly higher susceptibility to treatment with BSO, indicating that the reduction of the internal disulfide bonds of the ABP polyplex was abruptly decreased with the inhibition of GSH. These results indicate that the regulated release of pDNA through controlled polymer degradation is a critical step for efficient gene delivery.

Example 8—Stability of PEI, ABP, PAM-ABP G0 and PAM-ABP G1 Complexes

Figures 12, 13:
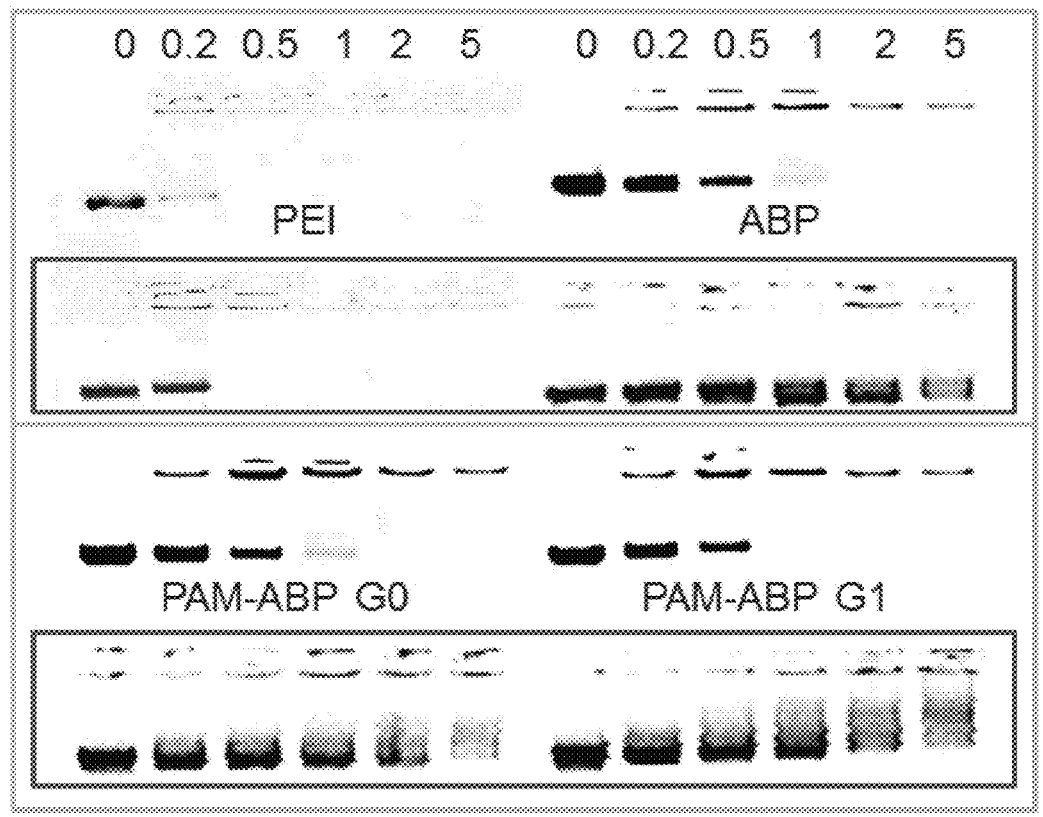
FIG. 12 shows gel retardation for PEI, ABP, PAM-ABP G0, and PAM-ABP G1 complexes at various weight ratios. The PAM-ABP G1 forms more stable complexes than ABP and PAM-ABP G0.
FIG. 13 shows the Zeta potential and size for exemplary embodiments of ABP, PAM-ABP G0, and PAM-ABP G1 complexes.

The stability of PEI, ABP, PAM-ABP G0 and PAM-ABP complexes were tested utilizing agarose gel retardation at various weight ratios of polymeric carrier to nucleic acid. bPEI 25 kDa is a non-degradable polymer and PAM-ABP is a degradable polymer. The PAM-ABP formed complexes with siRNA that were approximately 200 nm in diameter (surface charge: 20.5±4.89 mV). However, the size of complexes increased after DTT treatment for 2 h (surface charge: −36.3±16.8 mV). A reductive environment caused complete siRNA release from the PAM-ABP polyplexes while the PEI polyplexes was not affected (5.0 mM DTT condition. As can be seen in FIG. 12, the PAM-ABP G1 formed more stable polyplexes than ABP and PAM-ABP G0.

Example 9—In Vitro Transfection of Polyplexes

Various types of cells were seeded and treated with polyplexes/complexes containing luciferase in a similar manner as described in Example 4. The cells were than analyzed in a manner similar to that described in Example 4.

Figure 14:
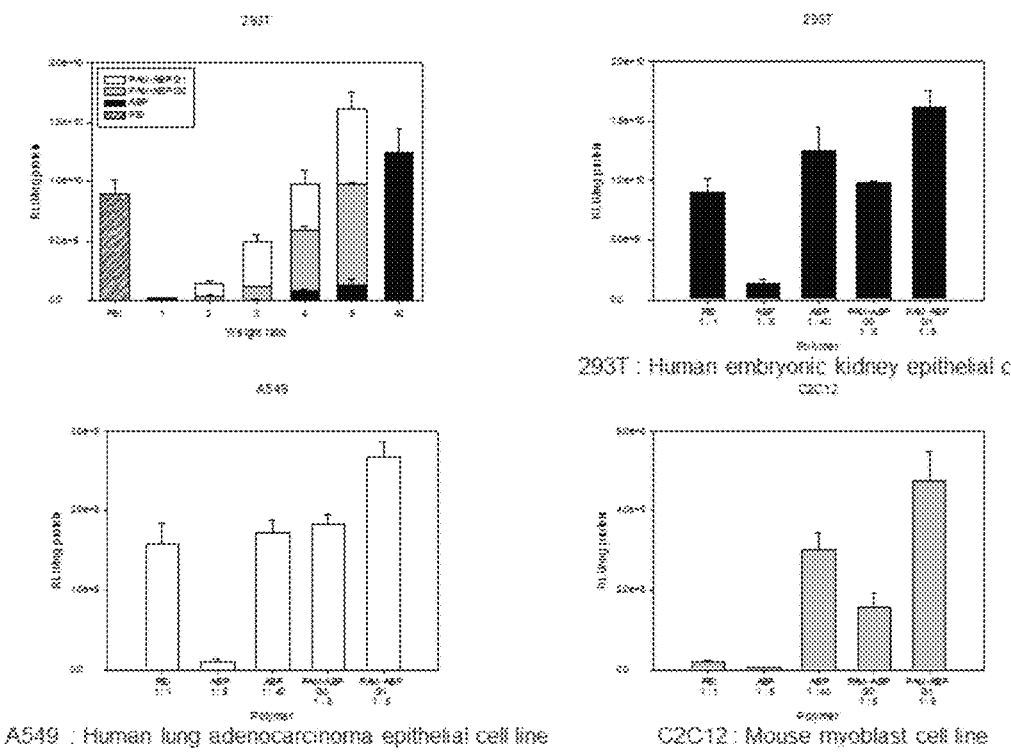
FIG. 14 shows the transfection efficiency of various polymeric carriers, including embodiments of the dendrimer polymeric carriers described herein.
Figure 15A:
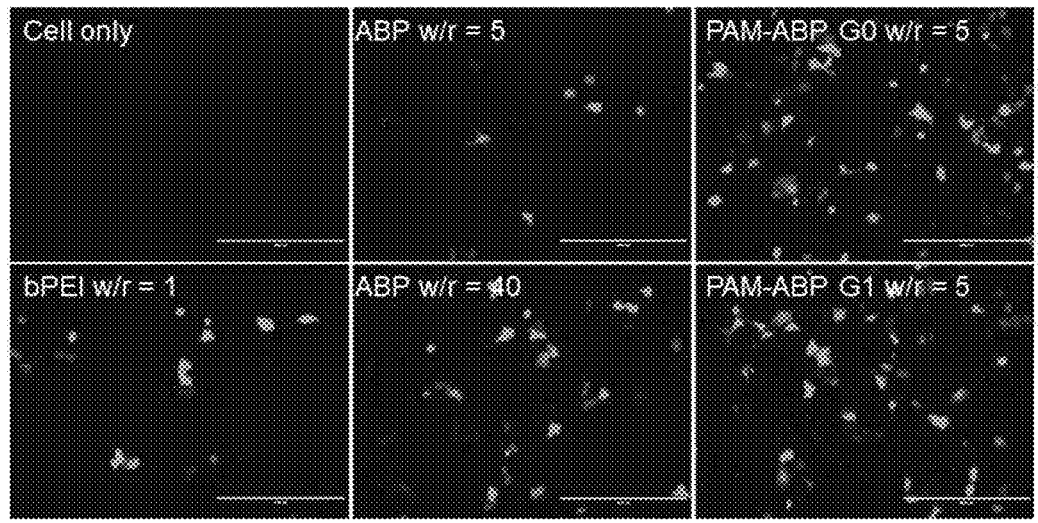
FIG. 15A-B show the GFP expression in A549 cells (15A) and C2C12 cells (15B) based on transfection using one embodiment of the complexes of the present invention. At a weight ratio of 5, PAM-ABP G0 and G1 showed higher cellular uptake than ABP and PEI complexes.
Figure 15B:
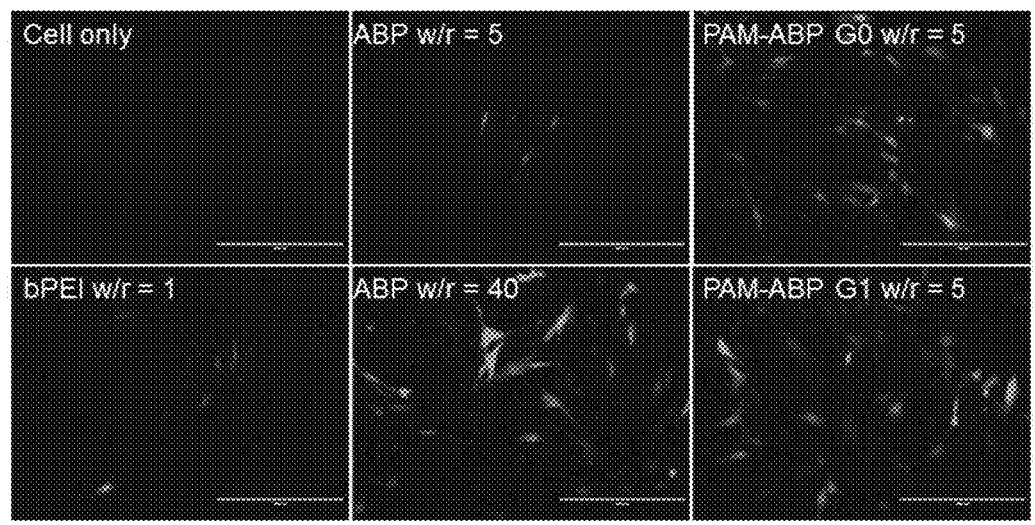

The transfection efficiency of the PEI, ABP, PAM-ABP G0, and PAM-ABP G1 were analyzed for each of the cell types of A549 (Human adenocarcinoma epithelial cell line) 293T (human embryonic kidney epithelial cells) and C2C12 (mouse myoblast cells). Various weight ratios of the polymeric carriers were analyzed. Luciferase expression tended to increase a dose-dependent manner for the ABP, PAM-ABP G0, and the PAM-ABP G1 complexes. FIG. 14 shows the transfection efficiency of various polymeric carriers, including embodiments of the dendrimer polymeric carriers described herein. FIGS. 15A and 15B show the GFP expression in A549 cells (15A) and C2C12 cells (15B). At a weight ratio of 5, PAM-ABP G0 and G1 showed higher cellular uptake than ABP and PEI complexes.

Example 10—Cytotoxicity of Polymers and Polyplexes

Figure 16A:
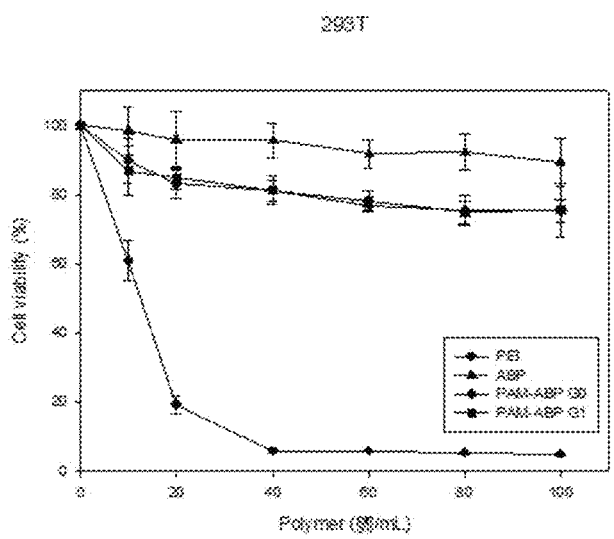
FIG. 16A-C shows the results of cytotoxicity assays for PEI, ABP, and PAM-ABP G0 and PAM-ABP G1 at various concentration of polymers in 293T cells (FIG. 16A), A549 cells (FIG. 16B), and in C2C12 cells (FIG. 16C). The results are reported in relative cell viability (%).
Figure 16B:
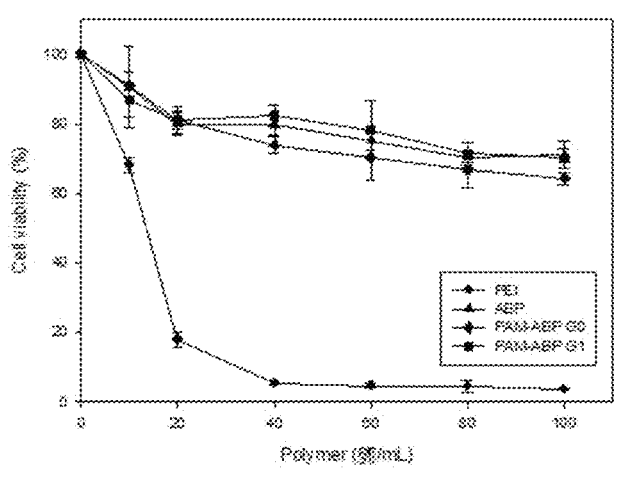
Figure 16C:
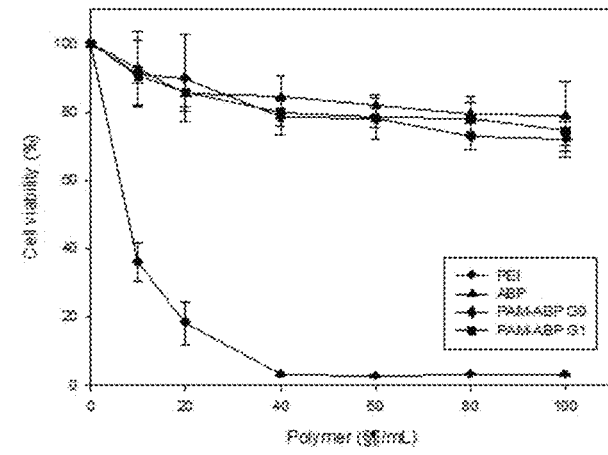

In order to evaluate the cytotoxicity of PEI, ABP, PAM-ABP G0, and PAM-ABP G1, an MTT assay was performed in a similar manner as described in Example 5. FIG. 16A-C shows the results of cytotoxicity assays for the various complexes at various concentration of polymers in 293T cells (FIG. 16A), A549 cells (FIG. 16B), and in C2C12 (FIG. 16C) cells. The results are reported in relative cell viability (%). As can be seen from the FIG. 16, the cytotoxicity of the ABP, PAM-ABP G0 and PAM-ABP G1 was similar.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A polymeric carrier for delivery of nucleic acid material to a cell, comprising: a dendrimer group having from 2 to 8 termini, each of the termini having an arginine-grafted bioreducible polymer attached thereto via an arginine residue of the arginine-grafted bioreducible polymer, wherein the arginine-grafted bioreducible polymer has the general structure of:

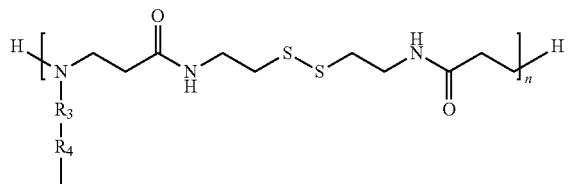

wherein n is 1 to 10 and wherein $R_3$ is $(CH_2)_m NH$, wherein m is about 1 to about 18; and
$R_4$ is an arginine residue.

2. The polymeric carrier of claim 1, wherein the dendrimer group has the general structure of:

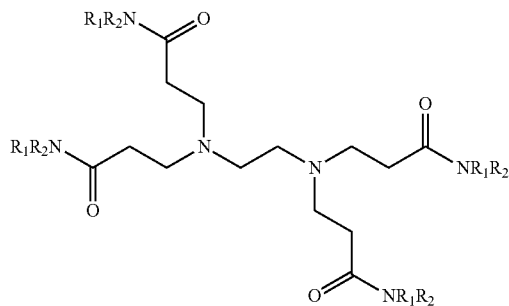

wherein each $R_1$ is individually selected from H, or $(CH_2)_2$—NH—$(CH_2)_2$—CO—NH—$(CH_2)_2$—NH—C$(NH_2)$—$(CH_2)_3$—S—S—$(CH_2)_2$—CO—NH-ABP, and each $R_2$ is individually selected from either $(CH_2)_2$—NH—C$(NH_2)$—$(CH_2)_3$—S—S—$(CH_2)_2$—CO—NH-ABP, or $(CH_2)_2$—NH—$(CH_2)_2$—CO—NH—$(CH_2)_2$—NH—C$(NH_2)$—$(CH_2)_3$—S—S—$(CH_2)_2$—CO—NH-ABP, wherein ABP has the general structure:

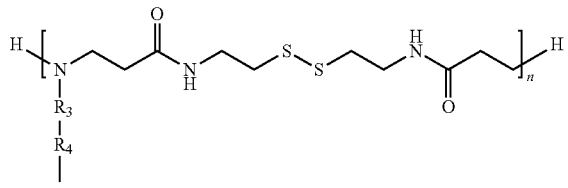

wherein n is 1 to 10 and wherein $R_3$ is $(CH_2)_m NH$, wherein m is about 1 to about 18; and
$R_4$ is an arginine residue.

3. The polymeric carrier of claim 1, wherein the dendrimer group has at least 4 termini.

4. The polymeric carrier of claim 1, wherein the dendrimer group has 8 termini.

5. The polymeric carrier of claim 1, wherein m is 6.

6. The polymeric carrier of claim 1, wherein n is 4 to 8.

7. The polymeric carrier of claim 1, wherein the polymeric carrier has the structure:

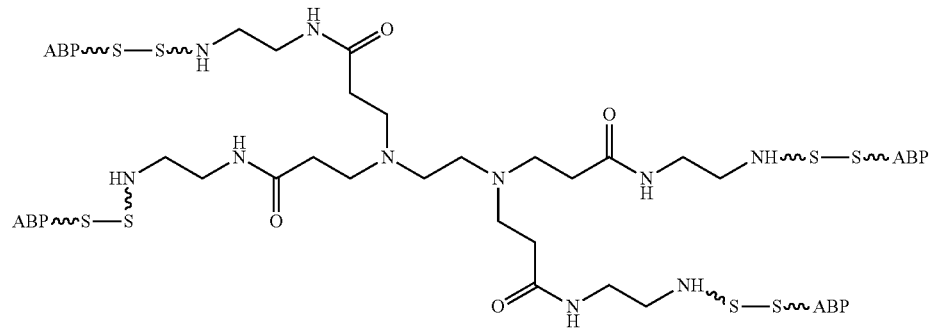

wherein

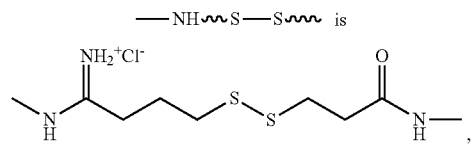 is

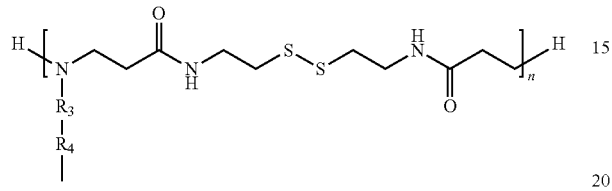

and wherein ABP has the general structure:

[structure shown]

wherein n is 1 to 10 and wherein $R_3$ is $(CH_2)_m NH$, wherein m is about 1 to about 18; and $R_4$ is an arginine residue.

8. The polymeric carrier of claim 1, wherein the polymeric carrier has a molecular weight of 5 kDa to about 50 kDa.

9. The polymeric carrier of claim 1, wherein the polymeric carrier has a molecular weight 9 kDa to about 50 kDa.

* * * * *